(12) United States Patent
Daines et al.

(10) Patent No.: US 6,214,856 B1
(45) Date of Patent: Apr. 10, 2001

(54) INDOLECARBOXAMIDES, PHARMACEUTICAL COMPOSITIONS AND METHODS OF INHIBITING CALPAIN

(75) Inventors: Robert A Daines, Lansdale; Kelvin Kin-Cheong Sham, King of Prussia, both of PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/380,317

(22) PCT Filed: Mar. 13, 1998

(86) PCT No.: PCT/US98/04873

§ 371 Date: Aug. 30, 1999

§ 102(e) Date: Aug. 30, 1999

(87) PCT Pub. No.: WO98/41092

PCT Pub. Date: Sep. 24, 1998

Related U.S. Application Data

(60) Provisional application No. 60/040,589, filed on Mar. 14, 1997.

(51) Int. Cl.$^7$ .................. A01N 43/38; A61K 31/405

(52) U.S. Cl. .................. 514/415; 514/419; 548/490; 548/491

(58) Field of Search .................. 514/415, 419; 548/490, 491

(56) References Cited

U.S. PATENT DOCUMENTS

| 5,106,847 | 4/1992 | Salituro et al. .................. 514/232.5 |
| 5,190,968 | 3/1993 | Gillard et al. .................. 514/419 |

FOREIGN PATENT DOCUMENTS 0 520 336  12/1992  (EP).

OTHER PUBLICATIONS

Patel, S. H., "Pharmacotherapy of Cognitive Impairment in Alzheimer's Disease: A Review", Journal of Geriatric Psychiatry and Neurology, vol. 8, 81–95, (1995).*

* cited by examiner

*Primary Examiner*—Dwayne C. Jones
(74) *Attorney, Agent, or Firm*—Loretta J. Henderson; Zoltan Kerekes; Stephen Venetianer

(57) ABSTRACT

Pharmaceutical compositions and methods of inhibiting calpain using novel indolecarboxamides are disclosed.

16 Claims, No Drawings

INDOLECARBOXAMIDES, PHARMACEUTICAL COMPOSITIONS AND METHODS OF INHIBITING CALPAIN

This application claims the benefit under 35 USC 120 of PCT/US98/04873 filed Mar. 13, 1998 under 35 USC 371, and under 35 USC 119(e) of provisional application No. 60/040,589, filed Mar. 14, 1997.

SUMMARY OF THE INVENTION

This invention relates to novel chemical compounds which are indolecarboxamides. The claimed pharmaceutical compositions and methods use those compounds as active ingredients to inhibit calpain and thus are useful in the treatment of, for example, neurodegenerative disorders, strokes and traumatic brain injury.

BACKGROUND OF THE INVENTION

Calpains are calcium—dependent cysteine proteases present in a variety of tissues and cells. Excessive activation of calpain provides a molecular link between ischaemia or injury induced by increases in intraneuronal calcium and pathological neuronal degeneration. If the elevated calcium levels are left uncontrolled, serious structural damage to neurons may result. Recent research has suggested that calpain activation may represent a final common pathway in many types of brain damage. Selective inhibition of calpain would, therefore, be an attractive therapeutic approach in the treatment of neurodegenerative diseases. Exemplary of these diseases would be myocardial ischaemia, cerebral ischaemia, muscular dystrophy, stroke, Alzheimer's disease, or traumatic brain injury. The compounds of this invention may also be useful in the treatment of cataracts and platelet aggregation.

DETAILED DESCRIPTION OF THE INVENTION

The compounds which are the active ingredients of the pharmaceutical compositions and methods of this invention are represented by the following formula:

Formula I

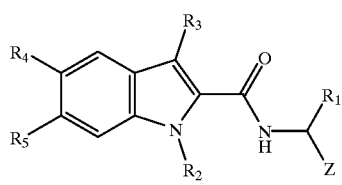

in which:

$R_1$ is $CH_2Ph$, $CH_2CH(CH_3)_2$, or $CH_2CH_2CH_2CH_2NR_6$, $R_7$;

Z is CHO, $COCH_2F$, COCOOH, COCONH-alkyl, COCOO-alkyl, $COCO(CH_2)_n$-aryl, $COCONHCH(R_1)$ COOH, or $COCH_2O$-(3-phenylisoxazol-5-yl);

n=1–6;

$R_2$ is H, $CH_3$, $CH_2Ph$, $CH_2$-pyridine, $CH_3SO_2$, $CF_3SO_2$, or $PhSO_2$;

$R_3$ is H, $CH_3$, or lower alkyl;

$R_4$ and $R_5$ are independently H, halo, lower alkyl, lower alkoxy, or benzyloxy;

$R_6$ is $COOCH_2Ph$, $COOCH_2$-pyridine, CO-aryl, $SO_2CH_3$, $SO_2CF_3$, $SO_2$-aryl, H, or lower alkyl; and $R_7$ is H, or lower alkyl, provided that when Z is CHO and $R_3$ is other than H, then $R_2$ is not H, or a pharmaceutically acceptable salt thereof.

Preferred compounds are those where the sterochemistry at the $R_1$ group corresponds to that of the naturally occurring amino acids. Also preferred are those compounds where $R_1$ is $CH_2Ph$ and Z is CHO.

The following preferred compounds are representative of the compounds of the invention:

(S)-N-(1-formyl-2-phenylethyl)1-methyl-2-indolecarboxamide;
(S)-N-(1-formyl-2-phenylethyl)-2-indolecaboxamide;
(S)-N-(1-formyl-2-phenylethyl)-5-methoxy-6-(phenylmethoxy)-2-indolecarboxamide;
(S)-5-bromo-N-(1-formyl-2-phenylethyl)-2-indolecarboxamide;
(S)-N-(1-formyl-2-phenylethyl)-1-(methylsulfonyl)-2-indolecarboxamide;
(S)-N-(1-formyl-2-phenylethyl)-1-phenylmethyl)-2-indolecarboxamide;
(S)-N-(1-formyl-2-phenylethyl)-6-methoxy-2-indolecarboxamide; and
(S)-N-(1-formyl-2-phenylethyl)-3-methyl-1-(phenylmethyl)-2-indolecarboxamide.

Compounds of Formula I are prepared by the methods illustrated in Schemes 1 and 2.

Scheme 1

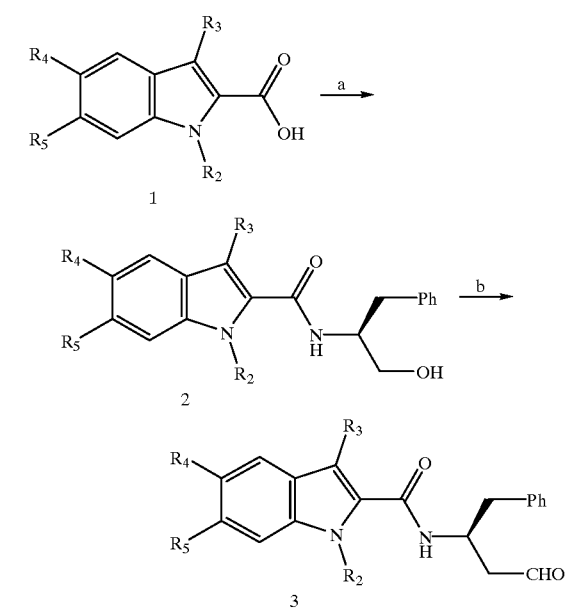

a) (S)-(−)-2-amino-3-phenylpropanol, EDC, HOBT, NMM, $CH_2Cl_2$;
b) Dess-Martin reagent, $CH_2Cl_2$.

The indole-2-carboxylic acids 1 (Scheme 1), whether prepared or commercially obtained, are converted to the amide alcohols 2 by standard coupling conditions (e.g., (S)-(−)-2-amino-3-phenylpropanol, 1-hydroxybenzotriazole hydrate (HOBT), 1-(3-dimethylaminopropyl)-3-ethylcarbodiimide hydrochloride (EDC), N-methylmorpholine (NMM), methylene chloride). Oxidation of 2 (the Dess-Martin reagent in methylene chloride is preferred, but not limiting) affords the aldehydes 3. This procedure can be repeated with a wide variety of substituted indole-2-carboxylic acids and with a wide variety of amino alcohol derivatives to obtain compounds with varying $R_1$ substituents.

Compounds of Formula I wherein the indole carboxylic acid is not commercially available are prepared by the method described in Scheme 2.

Scheme 2

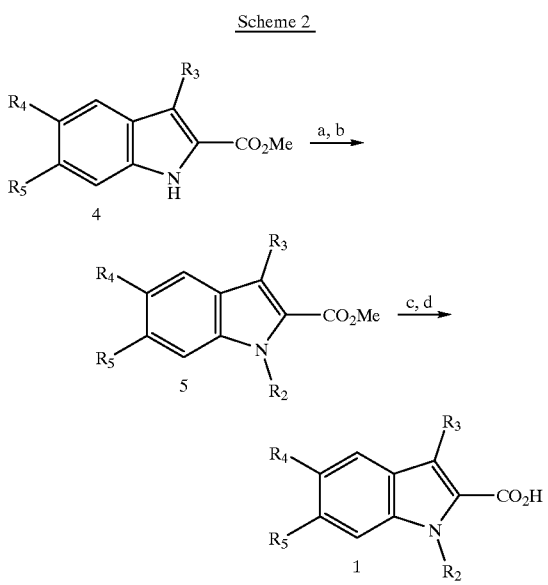

where $R_2 = CH_2Ph$ or $SO_2Me$
a) NaH, THF, 0–25° C.;
b) $PhCH_2Br$ or $MeSO_2Cl$;
c) 1NNaOH, MeOH, THF;
d) 10% HCl.

The commercially available indole esters 4 are treated with a base such as NaH to form the indole anion. This is then reacted with either an alkylating agent such as, but not limited to, benzyl bromide or a sulfonylating agent such as, but not limited to, methanesulfonyl chloride to provide the N-protected compounds 5. The ester is then hydrolyzed under standard conditions using NaOH to provide the desired indole 2-carboxylic acids 1. The acids 1 are then converted to the desired final compounds according to Scheme 1. For the cases where the indole ester 5 is commercially available, these compounds are converted directly to the acids 1 as described above.

Although these methods illustrate the preparation of compounds for which Z is CHO, alternative "enzyme reactive groups" can be substituted as has been extensively described in the literature (*J. Med. Chem.*, 1994, 37, 2918–2929; *J. Med. Chem.*, 1993, 36, 3472–3480; *J. Med. Chem.*, 1990, 33, 11–13; *Biochem. J.*, 1986, 239, 633–640; *J. Med. Chem.*, 1992, 35, 216–220). In addition, these methods are not intended to limit the scope of the possible $R_1$ groups which can be readily derived from any amino alcohol or amino acid by methods well known in the art.

Also included in the scope of the present invention are pharmaceutically acceptable salts of the compounds of Formula I. Preferred salts include, but are not limited to, hydrochloride, hydrobromide, citrate, tartrate, malate, maleate, lactate, gluctose 1,6-diphosphate, phosphate, succinate, sulfate, aspartate, adipate, methanesulfonate, lauryl sulfate, diguaiacyl phosphate, diacetyl sulfate, glutamate, edetate, ethylene diamine, sodium, potassium, calcium and ethanolamine salts. Such salts are prepared according to standard procedures well known in the art.

The pharmaceutical activity of the compounds of this invention is demonstrated by inhibition of calpain in vitro by the assay procedure described by Sasaki et al., *J. Biol. Chem.* 1984, 259, 12489–12494. The assays were performed using synthetic fluorogenic substrates. Inhibition of enzyme activity was calculated on the percent decrease in the rate of substrate hydrolysis in the presence of inhibitor relative to the rate in its absence. $IC_{50s}$(nM) were calculated. Table 1 demonstrates the results of testing representative compounds of Formula I.

TABLE 1

| $R_1$ | Z | $R_2$ | $R_3$ | $R_4$ | $R_5$ | $IC_{50}$(nM) |
|---|---|---|---|---|---|---|
| Ph | CHO | $CH_3$ | H | H | H | 500 |
| Ph | CHO | H | H | H | H | 600 |
| Ph | CHO | H | H | $CH_3O$ | $PhCH_2O$ | 135 |
| Ph | CHO | H | H | Br | H | 230 |
| Ph | CHO | $CH_3SO_2$ | H | H | H | 600 |
| Ph | CHO | $PhCH_2$ | H | H | H | 500 |
| Ph | CHO | H | H | H | $CH_3O$ | 600 |
| Ph | CHO | $PhCH_2$ | $CH_3$ | H | H | 30 |

The above results clearly indicate that all compounds tested exhibited significant inhibition of calpain.

The pharmaceutical compositions of this invention employed to inhibit calpain comprise a pharmaceutical carrier and as the active ingredient a compound of Formula I. The active ingredient will be present in the compositions of this invention in an effective amount to inhibit calpain. Preferably, the compositions contain the active ingredient of Formula I in an amount of from about 0.1 mg to about 250 mg, advantageously from about 25 mg to about 150 mg per dosage unit.

The pharmaceutical carrier may be, for example, a solid or liquid. Exemplary of solid carriers are lactose, magnesium stearate, sucrose, talc, stearic acid, gelatin, agar or acacia. Exemplary of liquid carriers are syrups, peanut oil, olive oil, propylene glycol, polyethylene glycol and water.

A wide variety of pharmaceutical forms may be employed. Thus, if a solid carrier is used, the preparation can be tabletted or placed in a hard gelatin capsule. If a liquid carrier is used, the preparation may be in the form of a soft gelatin capsule, placed in an ampule, a liquid suspension, syrup or suspension.

Preferably, parenteral solutions or suspensions are employed. They comprise the active compound in a sterile aqueous or oil carrier such as, for example, peanut oil, polyethylene glycol or polyvinyl pyrolidone. Preferably, such solutions contain the active compound in the range of 0.1 to 140 mg/kg of body weight of the patient to whom it will be administered. The sterile parenteral solutions may also contain additives such as, for example, preservatives such as benzyl alcohol and buffering agents to bring the injectable preparation to a satisfactory pH. Stabilizing agents such as ascorbic acid or sodium bisulfate may also be employed. DMSO or alcoholic solvents may be used to aid in the solubility and penetration of the calpain inhibitor.

The sterile aqueous solutions can also be lyophilized and reconstituted prior to administration.

The parenteral solution may be administered subcutaneously, intravenously, intramuscularly, interperitoneally, intrasternally or by intrathecal injection directly into the central nervous system.

The pharmaceutical compositions are prepared by conventional techniques involving procedures such as mixing, granulating and compressing to dissolve the ingredients as appropriate to the desired preparation.

The method of inhibiting calpain according to this invention comprises administering to an animal or human in an amount sufficient to inhibit calpain a compound of Formula I.

Preferably the compounds of Formula I are administered in conventional dosage unit forms prepared by combining an appropriate dose of the compound with standard pharmaceutical carriers.

Most preferably, the active ingredients of Formula I will be administered in a daily dosage regimen of from about 2.0 mg to about 1.0 g, most preferably from about 50 mg to about 400 mg. Advantageously, equal doses will be administered two to four times a day. When the administration is carried out as described above, inhibition of calpain is produced.

The route of administration of the pharmaceutical compositions of this invention and in accordance with the methods of this invention is internal, more specifically either oral or preferably parenteral, in an amount sufficient to produce the desired biological activity.

The following examples are not limiting but are illustrative of the compounds and compositions of this invention and the process for their preparation.

EXAMPLE 1

Preparation of (S)-N-(1-formyl-2-phenylethyl)-1-methyl-2-indolecarboxamide a) (S)-N-(1-Hydroxymethyl-2-phenylethyl)-1-methyl-2-indolecarboxamide To a stirred solution of 1-methyl-2-indolecarboxylic acid (100 mg, 0.57 mmol) in methylene chloride (1 mL) was added N-methylmorpholine (0.063 mL, 0.57 mmol) followed by (S)-(−)-2-amino-3-phenyl-1-propanol (86 mg, 0.57 mmol), 1-hydroxybenzotriazole hydrate (81 mg, 0.60 mmol), and 1-(3-dimethylaminopropyl)-3-ethylcarbodiimide hydrochloride (120 mg, 0.63 mmol). The resulting mixture was stirred at room temperature for 20 h. The reaction was diluted with methylene chloride and washed sequentially with 10% citric acid, saturated $NaHCO_3$, water, and brine. The organic layer was dried over $Na_2SO_4$ and concentrated in vacuo to give a crude oil. Trituration of the crude oil with methanol and diethyl ether afforded the title compound (68%, 119.7 mg) as an off-white solid. MS (ES) m/e 309.4 $[M+H]^+$.

b) (S)-N-(1-Formyl-2-phenylethyl)-1-methyl-2-indolecarboxamide

To a solution of the compound of Example 1(a) (90 mg, 0.29 mmol) in methylene chloride (7 mL) was added 1,1,1-triacetoxy-1,1-dihydro-1,2-benziodoxol-3(1H)-one (Dess-Martin periodinane) (129 mg, 0.3 mmol). The resulting mixture was stirred at room temperature for 1h and quenched with 10% sodium thiosulfate solution. After stirring for 10 minutes, the reaction was diluted with methylene chloride and washed with 10% sodium thiosulfate solution (3x), saturated $NaHCO_3$, and brine. The organic layer was dried over $Na_2SO_4$ and concentrated in vacuo to give a crude oil. Trituration of the crude oil with ethyl acetate/diethyl ether/petroleum ether afforded the title compound (49%, 43.1 mg) as a white solid MS (ES) m/e 307.4 $[M+H]^+$.

EXAMPLE 2

Preparation of (S)-N-(1-formyl-2-phenylethyl)-2-indolecarboxamide

Following the procedures of Example 1(a) and 1(b), except substituting 2-indolecarboxylic acid for 1-methyl-2-indolecarboxylic acid, the title compound was prepared as a white solid. MS (ES) m/e 293.3 $[M+H]^+$.

EXAMPLE 3

Preparation of (S)-N-(1-formyl-2-phenylethyl)-5-methoxy-6-(phenylmethoxy)-2-indolecarboxamide Following the procedures of Example 1(a) and 1(b), except substituting 5-methoxy-6-(phenylmethoxy)-2-indolecarboxylic acid for 1-methyl-2-indole-carboxylic acid, the title compound was prepared as a yellow solid. MS (ES) m/e 429.3 $[M+H]^+$.

EXAMPLE 4

Preparation of (S)-5-bromo-N-(1-formyl-2-phenylethyl)-2-indolecarboxamide

Following the procedures of Example 1(a) and 1(b), except substituting 5-bromo-2-indolecarboxylic acid for 1-methyl-2-indolecarboxylic acid, the title compound was prepared as a tan solid. MS (ES) m/e 371.3 $[M+H]^+$.

EXAMPLE 5

Preparation of (S)-N-(1-formyl-2-phenylethyl)-1-(methylsulfonyl)-2-indolecarboxamide a) Ethyl 1-(methylsulfonyl)-2-indolecarboxylate A solution of ethyl-2-indolecarboxylate (500 mg, 2.64 mmol) in dry THF (5 mL) under an argon atmosphere was cooled to 0° C. and treated with sodium hydride (116 mg, 2.90 mmol). After stirring at room temperature for 5 minutes, the reaction was cooled to 0° C. and treated with methanesulfonyl chloride (0.23 mL, 2.90 mmol). The resulting mixture was gradually warmed to room temperature and stirred for 20 h. The reaction was quenched with saturated $NaHCO_3$ and diluted with ethyl acetate. The organic layer was washed with water and brine, dried over $Na_2SO_4$, and concentrated in vacuo. The resulting golden yellow oil was chromatographed over silica gel eluting with 5%, 10%, and 15% ethyl acetate/hexane to provide the title compound (79%, 556.6 mg) as a cream solid. $^1$H NMR (400 MHz, $CDCl_3$) δ8.05 (d, 1H), 7.65 (d, 1H), 744 (t, 1H), 7.31 (m, 2H), 4.42 (q, 2H), 3.71 (s, 3H), 1.42 (t, 3H).

b) 1-Methylsulfonyl)-2-indolecarboxylic Acid

A solution of the compound of Example 5(a) (456.6 mg, 1.71 mmol) in THF (6 mL) and methanol (3 mL), was treated with aqueous 1N NaOH (3.42 mL, 3.42 mmol) and stirred at room temperature for 20 h. The reaction mixture was acidified with 10% HCl (to pH 3) and the solvent was removed at reduced pressure. The resulting slurry was diluted with methylene chloride and washed with brine. The organic layer was dried over $Na_2SO_4$ and concentrated in vacuo to provide an off-white solid. Trituration with diethyl ether afforded the title compound (57%, 234 mg) as a white solid. MS (ES) m/e 239.1 $[M]^+$.

c) (S)-N-(1-Hydroxymethyl-2-phenylethyl)-1-(methylsulfonyl)-2-indolecarboxamide

Following the procedure of Example 1(a), except substituting the compound of Example 5(b) for 1-methyl-2-indolecarboxylic acid, the title compound was prepared as a viscous colorless oil. MS (ES) m/e 373.4 $[M+H]^+$.

d) (S)-N-(1-Formyl-2-phenylethyl)-1-(methylsulfonyl)-2-indolecarboxamide

Following the procedure of Example 1(b), except substituting the compound of Example 5(c) for the compound of Example 1(a), the title compound was prepared as an off-white solid. MS (ES) m/e 371.3 [M+H]⁺.

EXAMPLE 6

Preparation of (S)-N-(1-formyl-2-phenylethyl)-1-(phenylmethyl)-2-indolecarboxamide Following the procedures of Examples 5(a)–(d) respectively, except substituting benzyl bromide for methanesulfonyl chloride, the title compound was prepared as a white solid. MS (ES) m/e 383.5 [M+H]⁺.

EXAMPLE 7

Preparation of (S)-N-(1-formyl-2-phenylethyl)-6-methoxy-2-indolecarboxamide

Following the procedures of Examples 5(b)–(d) respectively, except substituting methyl 6methoxy-2-indolecarboxylate for ethyl 2-indolecarboxylate, the title compound was prepared as a beige solid. MS (ES) m/e 323.3 [M+H]⁺.

EXAMPLE 8

Preparation of (S)-N-(1-formyl-2-phenylethyl)-3-methyl-1-(phenylmethyl)-2-indolecarboxamide Following the procedures of Examples 5(a)–(d) respectively, except substituting methyl 3-methyl-2-indolecarboxylate for ethyl 2-indolecarboxylate and benzyl bromide for methanesulfonyl chloride, the title compound was prepared as a cream solid. MS (ES) m/e 397.3 [M+H]⁺.

EXAMPLE 9

| Ingredients | Mg./Capsule |
| --- | --- |
| (S)-N-(1-formyl-2-phenylethyl)-3-methyl-1-(phenylmethyl)-2-indolecarboxamide | 250.00 |
| Magnesium Stearate | 5.00 |
| Lactose | 100.00 |

The ingredients are thoroughly mixed and filled into a hard gelatin capsule.

EXAMPLE 10

| Ingredients | Mg./Tablet |
| --- | --- |
| (S)-N-(1-formyl-2-phenylethyl)-5-methoxy-6-(phenylmethoxy)-2-indolecarboxamide | 100.00 |
| Lactose | 250.00 |
| Starch | 13.00 |
| Talc | 5.00 |
| Magnesium Stearate | 2.50 |

The lactose and indolecarboxamide are mixed and granulated with hot 10% gelatin. The granules are dried and passed through a #20 mesh screen. The granules are then mixed with the starch, talc and magnesium stearate and compressed into a tablet.

One tablet is administered four times a day to mammals for treatment of neurodegenerative diseases.

EXAMPLE 11

| Ingredients | Amounts/Mg. |
| --- | --- |
| (S)-N-(1-formyl-2-phenylethyl)-3-methyl-1-(phenylmethyl)-2-indolecarboxamide | 75.00 |
| DMSO | 500.00 |
| Sodium Chloride | 375.00 |
| Sodium Bisulfite | 100.00 |
| Water for Injection q.s. | 100 ml |

The indolecarboxamide is dissolved in the DMSO and 50% of the water. The salts are thoroughly dissolved and the volume is brought up to 100 ml. The solution is then filtered and filled into ampules and autoclaved.

EXAMPLE 12

| Ingredients | Amounts/Mg. |
| --- | --- |
| (S)-N-(1-formyl-2-phenylethyl)-5-methoxy-6-(phenylmethoxy)-2-indolecarboxamide | 150.00 |
| Peanut Oil | 300.00 |

The ingredients are mixed to a thick slurry and filled into soft gelatin capsules. One capsule is administered orally to mammals for treatment of neurodegenerative diseases.

What is claimed is:

1. A compound of the formula:

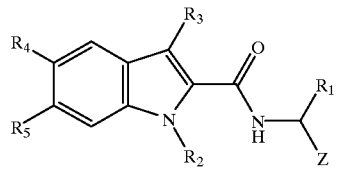

in which:

$R_1$ is $CH_2Ph$, $CH_2CH(CH_3)_2$, or $CH_2CH_2CH_2CH_2NR_6$, $R_7$;

Z is CHO, $COCH_2F$, COCOOH, COCONH-alkyl, COCOO-alkyl, $COCO(CH_2)_n$-aryl, $COCONHCH(R_1)$ COOH, or $COCH_2O$-(3-phenylisoxazol-5-yl);

n=1–6;

$R_2$ is H, $CH_3$, $CH_2Ph$, $CH_2$-pyridine, $CH_3SO_2$, $CF_3SO_2$, or $PhSO_2$;

$R_3$ is H, $CH_3$, or lower alkyl;

$R_4$ and $R_5$ are independently H, halo, lower alkyl, lower alkoxy, or benzyloxy;

$R_6$ is $COOCH_2Ph$, $COOCH_2$-pyridine, CO-aryl, $SO_2CH_3$, $SO_2CF_3$, $SO_2$-aryl, H, or lower alkyl; and $R_7$ is H, or lower alkyl, provided that when Z is CHO and $R_3$ is other than H, then $R_2$ is not H, or a pharmaceutically acceptable salt thereof.

2. A compound of claim 1 in which the C-5 sterochemistry is S.

3. A compound of claim 2 in which $R_1$ is $CH_2Ph$ and Z is CHO.

4. A compound of claim 3 being (S-N-(1-formyl-2-phenylethyl)-1-methyl-2-indolecarboxamide.

5. A compound of claim 3 being (S)-N-(1-formyl-2-phenylethyl)-2-indolecarboxamide.

6. A compound of claim 3 being (S)-N-(1-formyl-2-phenylethyl)-5-methoxy-6-(phenylmethoxy)-2-indolecarboxamide.

7. A compound of claim 3 being (S)-5-bromo-N-(1-formyl-2-phenylethyl)-2-indolecarboxamide.

8. A compound of claim 3 being (S)-N-(1-formyl-2-phenylethyl)-1-(methyl-sulfonyl)-2-indolecarboxamide.

9. A compound of claim 3 being (S)-N-(1-formyl-2-phenylethyl)-1-(phenylmethyl)-2-indolecarboxamide.

10. A compound of claim 3 being (S)-N-(1-formyl-2-phenylethyl)-6-methoxy-2-indolecarboxamide.

11. A compound of claim 3 being (S)-N-(1-formyl-2-phenylethyl)-3-methyl-(1-phenylmethyl)-2-indolecarboxamide.

12. A pharmaceutical composition in dosage unit form for inhibiting calpain comprising a pharmaceutical carrier and an effective amount of the compound as described in claim 1.

13. A method of inhibiting calpain which comprises administering to an animal or human in an amount sufficient to inhibit calpain a compound as described in claim 1.

14. A method of treating neurodegenerative diseases which comprises administering to an animal or human in need thereof orally or by injection a sufficient amount of a compound of claim 1.

15. The method of claim 13 wherein the amount is from about 50 to about 500 mg. of the compound per dosage unit and the administration is orally.

16. The method of claim 13 wherein the amount is from about 0.1 to 140 mg/kg of body weight of the animal or human and the administration is parenterally.

* * * * *